United States Patent [19]

Weber et al.

[11] 4,172,091

[45] Oct. 23, 1979

[54] PROCESS FOR THE MANUFACTURE OF β-(DIMETHYLAMINO)-PROPIONITRILE

[75] Inventors: Jürgen Weber, Oberhausen; Helmut Springer, Voerde; Boy Cornils; Hans Feichtinger, both of Dinslaken; Wolfgang Payer, Wesel, all of Fed. Rep. of Germany

[73] Assignee: Ruhrchemie Aktiengesellschaft, Oberhausen, Fed. Rep. of Germany

[21] Appl. No.: 883,757

[22] Filed: Mar. 6, 1978

[30] Foreign Application Priority Data

Mar. 8, 1977 [DE] Fed. Rep. of Germany ....... 2709966

[51] Int. Cl.² .................. C07C 120/00; C07C 121/43
[52] U.S. Cl. ............................................. 260/465.5 R
[58] Field of Search ................................ 260/465.5 R

[56] References Cited

U.S. PATENT DOCUMENTS 4,055,586 10/1977 Feichtinger et al. ......... 260/465.5 R

OTHER PUBLICATIONS

Nazarov et al., C.A., 51(1957), 15520b.
Sen et al., C.A., 57(1962), 4662a.
Yashunskii; C. A., 59(1963), 602f.
Moehring; C.A., 69(1968), 86410t.
Rouvier et al.; C.A., 75(1971), 48255n.

Primary Examiner—Joseph Paul Brust
Attorney, Agent, or Firm—Sprung, Felfe, Horn, Lynch & Kramer

[57] ABSTRACT

An improvement in a process for the manufacture of β-(dimethylamino)-propionitrile by contacting acrylonitrile with dimethylamine, the improvement residing in passing the reactants in countercurrent with respect to one another in a bubble column reactor and reacting them therein at a temperature between 25° and 80° C., preferably 40° to 60° C.

9 Claims, No Drawings

PROCESS FOR THE MANUFACTURE OF β-(DIMETHYLAMINO)-PROPIONITRILE

BACKGROUND OF THE INVENTION

1. Field of the Invention

This invention relates to a process for the manufacture of β-(dimethylamino)-propionitrile by reaction of acrylonitrile and dimethylamine. More especially, this invention relates to a process for reacting acrylonitrile and dimethylamine at mild reaction conditions in counter-current flow in a bubble column to obtain virtually quantitative yields of β-(dimethylamino)-propionitrile.

2. Discussion of the Prior Art

The manufacture of β-(dimethylamino)-propionitrile usually occurs via the addition of dimethylamine to acrylonitrile, corresponding to the following equation:

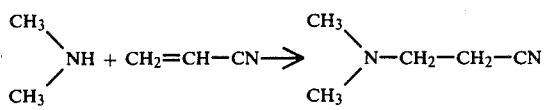

According to the JA Patent Application No. 72/03 809, gaseous dimethylamine is fed into acrylonitrile between 0° and 5° C. The reaction mixture is subsequently allowed to stand for one hour. β-(dimethylamino)-propionitrile is thereby obtained in 99 percent yield.

The disadvantage of this process lies in the necessity of maintaining the temperature between 0° and 5° C. This is very involved technically—making the economic efficiency of this process questionable.

It is known from DL-P No. 58 306 that dimethylamine and acrylonitrile can be reacted, for example in co-current in a recycle apparatus at 0° to 60° C., using the reaction product as solvent and diluent. However, with this method, β-(dimethylamino)-propionitrile is obtained in only a 94 percent yield.

It is an object of this invention, therefore, to provide a process for the manufacture of β-(dimethylamino)-propionitrile whereby the product is obtained in a high yield using a simple apparatus and mild reaction conditions.

SUMMARY OF THE INVENTION

Broadly, this invention contemplates an improvement in the process for preparing β-(dimethylamino)-propionitrile by contacting acrylonitrile with dimethylamine, the improvement residing in carrying out the process at a temperature between 25° and 80° C. in a bubble column reactor and feeding the reactants in countercurrent flow with respect to one another in said bubble column reactor.

The process is preferably carried out at a temperature between 40° and 60° C. and is preferably conducted continuously.

It could not be anticipated that the reaction partners would be converted almost quantitatively, while forming the required reaction product. A long after-treatment, necessary with the method in JA-Patent Application No. 72/03809, is avoided completely. It is also unnecessary to provide large reaction chambers, which only complicate the industrial production. The new process also makes it possible to work at temperatures which are easily regulated.

The bubble column used as reactor in this invention is of conventional design. A description of this type of reactor is found, for example in Ullmans Encyclopädie der technischen Chemie, Vol. 3, p. 369, (1973). According to the process of the invention, bubble column reactors which have a ratio of diameter to length of 1:5 to 1:20 are used.

The process is carried out very simply. Acrylonitrile is introduced at the top, dimethylamine is fed from below via a distributor (e.g. a frit designed as a feed inlet) into the reactor, which is heated to a temperature between 25° and 80° C., preferably 40° to 60° C. Acrylonitrile and dimethylamine must be introduced in such quantities that residence times of 20 to 120 minutes, preferably 30 to 60 minutes, are obtained. The mole ratio of dimethylamine to acrylonitrile lies between 1 to 1.5:1, preferably 1 to 1.05:1. The gaseous amine is almost completely absorbed at once and chemically bound, then immediately converted into the desired β-(dimethylamino)-propionitrile. The reaction product which leaves the bubble column reactor just above the distributor is a clear liquid, constituting nearly pure β-(dimethylamino)-propionitrile. This liquid requires no further purification and can be used in other reactions. It can, for example, be hydrogenated to the corresponding amine.

β-(dimethylamino)-propionitrile can be employed as stabilizer and as polymerization catalyst. Furthermore, it is a valuable precursor for the manufacture of biocides and detergents. β-(dimethylamino)-propionitrile, resulting from hydrogenation, has gained importance as an intermediate in the manufacture of biocides, additives for motor fuel, flame retardants, antistatics, antioxidants and corrosion inhibitors.

In order to more fully illustrate the nature of the invention and the manner of practicing the same, the following example is presented:

EXAMPLE

The reaction occurred in a reaction tube which had an inside diameter of 36 mm and was 70 cm long. At the lower end there was a glass frit G4, which functioned as distributor. The total volume of the tube was 700 ml, the effective reaction volume, i.e., the space used during the reaction was 400 ml.

226 g of gaseous dimethylamine were fed hourly via the glass frit into the reactor at a temperature of 50° C. Each hour, 261 g of acrylonitrile were introduced at the top. A complete absorption of the amine occurred just 4 cm above the floor of the frit. While maintaining a constant reactor volume, the reaction product was drawn off above the glass frit at a rate of 574 ml/hour—corresponding to a residence time of 42 minutes. The space velocity was 1.435. The gas chromatographic analysis of the crude product showed a 99.1 percent β-(dimethylamino)-propionitrile content with 0.9 percent dimethylamine. With a total conversion of acrylonitrile, a selectivity of over 99.9 percent was achieved.

The reaction product can then be directly hydrogenated according to the usual method.

What is claimed is:

1. In a process for the manufacture of β-(dimethylamino)-propionitrile wherein acrylonitrile is contacted with dimethylamine, the improvement which comprises carrying out the process at a temperature of 25° to 80° C. in a bubble column reactor and feeding the reactants therein in countercurrent flow with respect to one another.

2. A process according to claim 1 wherein the process is carried out at a temperature of 40° to 60° C.

3. A process according to claim 1 wherein the residence time of the reactants in the reactor is 20 to 120 minutes.

4. A process according to claim 3 wherein the residence time of the reactants in the reactor is 30 to 60 minutes.

5. A process according to claim 1 wherein the dimethylamine and acrylonitrile are fed into the bubble column reactor in a mole ratio of 1–1.5 moles dimethylamine per mole acrylonitrile.

6. The process according to claim 5 wherein the mole ratio of dimethylamine to acrylonitrile is 1–1.05:1.

7. A process according to claim 1 which is carried out continuously.

8. A process according to claim 1 wherein the acrylonitrile is fed into the top of said bubble column reactor and gaseous dimethylamine is fed into the bottom of the reactor and allowed to pass upwardly in countercurrent flow to downwardly moving acrylonitrile.

9. A process according to claim 8 carried out in a bubble column reactor having a ratio of diameter to length of 1:5–20.

* * * * *